United States Patent [19]

Rosenberg

[11] Patent Number: 4,710,171

[45] Date of Patent: Dec. 1, 1987

[54] NEEDLE DEPTH SETTING SHEATH ASSEMBLY AND NEEDLE STOP

[75] Inventor: Helmut W. G. Rosenberg, McHenry, Ill.

[73] Assignee: The Kendall Company, Boston, Mass.

[21] Appl. No.: 872,352

[22] Filed: Jun. 9, 1986

[51] Int. Cl.$^4$ .............................................. A61M 5/00
[52] U.S. Cl. ................................................... 604/117
[58] Field of Search ......................... 604/117, 187, 198

[56] References Cited

U.S. PATENT DOCUMENTS

| 268,996 | 12/1882 | Brinkerhoff | 604/198 |
|---|---|---|---|
| 2,559,474 | 7/1951 | Son | 604/117 |
| 2,569,901 | 10/1951 | Richard | 604/117 |

FOREIGN PATENT DOCUMENTS 1022758  1/1958  Fed. Rep. of Germany ...... 604/117

Primary Examiner—John D. Yasko
Attorney, Agent, or Firm—D. N. Halgren

[57] ABSTRACT

A biological needle depth setting arrangement comprising a locking assembly tightenable about the needle barrel. A sheath with graduations therein permits the needle depth to be adjusted accurately. An elastomer bushing is compressible about the needle barrel, and the bushing is prevented from dislocation through a screw-hub arrangement.

4 Claims, 3 Drawing Figures

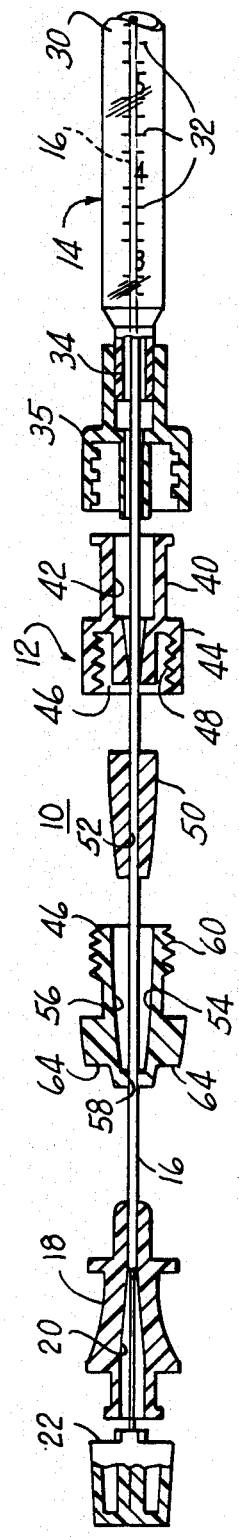
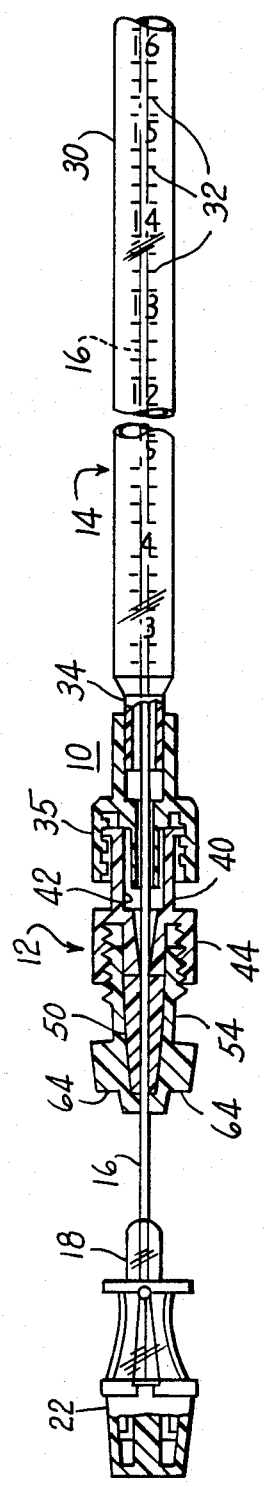
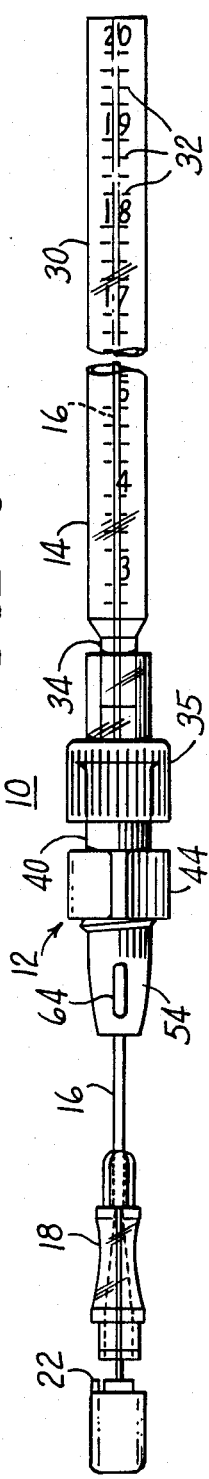

NEEDLE DEPTH SETTING SHEATH ASSEMBLY AND NEEDLE STOP

BACKGROUND OF THE INVENTION

1. Field of the Invention

The present invention relates to medical instruments such as needle assemblies, and more particularly to depth setting mechanisms for such needle assemblies.

2. Prior Art

A major medical problem exists where about 13 million Americans suffer from kidney and urinary tract-related diseases. Currently, over 200,000 Americans are hospitalized each year for kidney stones. All patients with a renal or upper ureteral calculi requiring surgical removal are candidates for percutaneous ultrasonic liphotripsy, a procedure by which kidney stones are fragmented with ultrasonic energy and extracted through an endoscope. To perform the percutaneous ultrasonic liphotripsy, a needle and thin guide wire are inserted through a skin puncture and are advanced under fluoroscopy through the renal pharemchyma into a middle or lower calix. In some cases the operation is also visualized with ultrasound by itself or in combination with the fluoroscopy. The needle being inserted has to be inserted only to a specific depth. In one form of the prior art, a sterile tape is placed on a teflon-sheet needle at the measured distance from the needle tip. The needle would then be inserted up the tape prior to the subsequent introduction of catheters to facilitate kidney drainage and the like. Needless to say, placing a tape circumferentially above a needle and injecting that needle into a patient could certainly be deleterious to the health of a patient.

A number of different devices have been shown wherein the depth of a needle may be preselected. U.S. Pat. No. 4,356,822 to Winstead-Hall shows an arrangement of locking ribs. The series of ribs engage one another when the plunger is rotated so as to strike thereagainst. This concept however, only allows specific projections of the needle, there is not an infinite number of depth settings available.

U.S. Pat. No. 3,356,089 to Francis shows a long needle joined in the forward end of the medication barrel and generally closely surrounded by a sheath so that the controlled advancing and retracting of the medication barrel a selected distance is permitted.

A further depth setting arrangement is shown in U.S. Pat. No. 2,338,800 to Burke, wherein a locking guide is engagable on the end of a needle. The locking guide comprises a plate which prevents further insertion of the needle into the patient. A further U.S. Pat. No. 4,332,248 to DeVitas has a support guide which provides an aid to inserting a needle into its desired depth. An unusual depth setting device is shown in U.S. Pat. No. 3,538,916 to Wiles which is described as an injection pistol having a proximal end of a shaft which has a threaded means on the end of a shaft which is adjustable to pre-select the depth to which the needle will advance into the patient.

An adapter assembly shown in U.S. Pat. No. 4,187,848 enables a syringe and a catheter to be locked together, to permit a liquid to be pumped through the adapter to the catheter. No suggestion is made of using the adapter as a locking device on a barrel to facilitate depth setting thereof with a sheath.

It is an object of the present invention to overcome the limitations of the prior art.

It is a further object of the present invention to provide a depth setting arrangement for a needle which is self contained and easy to set.

It is still a further object of the present invention to provide a depth setting apparatus which is sterilizable within its own container.

BRIEF SUMMARY OF THE INVENTION

A needle assembly having depth setting facilities therewith for use particularly in a percutaneous nephrostomy procedure has a needle at its proximal end. The needle has an extended hollow shaft which extends to a hub at its proximal end. The needle hub is hollow so as to provide fluid communication therethrough.

A trocar is disposable through the hub and into the needle so when it is fully extended therethrough the distalmost end of the trocar completely and smoothly blocks the open distalmost end of the needle.

The needle and its assembly is disposed within a sheath for its full length. The sheath has graduations marked on its surface thereof. The proximal end of the sheath may be in a slipfit relationship with a Luer lock and/or a connector means on the needle stop assembly. The needle stop assembly further comprises a hub having a central abutment. The hub is threadably engagable with a cone-shaped housing. The cone-shaped housing has a pair of tabs which permit or facilitate the engagement of the housing with the hub. A cone-shaped elastomer bushing is disposed about the needle, between the hub and the cone-shaped housing.

In operation of the depth setting arrangement, the needle and trocar are withdrawn in the sheath so as the proximalmost end may match up with the desired depth as set or stated on the graduations of the sheath. When the tip of the needle reaches the desired point of the graduations, the cone-shaped housing is screwed into the hub which is fitted onto the distalmost end of the sheath or to the Luer lock which is fitted onto the sheath. As the cone-shaped housing tightens into the hub it compresses the elastomer bushing peripherally inwardly about the needle. The radially inwardly directed pressure of the elastomer on the surface of the needle causes it to lock onto that peripheral location. The sheath surrounding the needle may then be withdrawn therefrom, thus effectuating the depth setting thereof by the hub being fixed to the needle. The needle may be driven into the patient at a depth no greater than the connector assembly (hub) which was formerly disposed on the proximalmost end of the sheath assembly.

Thus it may be seen that a simple, easy to manufacture economical and sterilizable locking assembly may be made and disposed about a needle which is usable in medical situations where the depth of needle insertion is of critical significance.

BRIEF DESCRIPTION OF THE DRAWINGS

The objects and advantages of the present invention will become more apparent in conjunction with the following drawings in which:

FIG. 1 is an exploded side elevational sectional view of a needle having a depth setting assembly and a needle stop therewith;

FIG. 2 is a partial sectional side elevational view of the needle assembly as shown in FIG. 1; and FIG. 3 is a side elevational view of the complete needle assembly.

BRIEF DESCRIPTION OF THE DRAWINGS

Referring now to the drawings in detail and particularly to FIG. 1 there is shown a needle assembly 10 including a needle stop assembly 12 and a depth setting arrangement 14. The needle assembly 10 comprises a hollow needle shaft 16 of extended length. The hollow needle 16 is attached to a needle hub 18 at its proximalmost end. The needle hub 18 is hollow and has a bore 20 therethrough which is in fluid communication with the hollow portion of the needle 16.

A trocar 22 is disposed through the needle hub 18 and the hollow needle 16 and has a distalmost end which is contiguous with the distalmost end of the needle 16. The orientation of the distalmost end of the trocar with the distalmost end of the needle 16 presents a solid smooth surface thereat.

A sheath 30 is disposed over the extended body of the needle 16. The sheath 30 has a plurality of graduations thereon 32. The graduations 32 act as a scale against which the depth of the needle is to be measured. The sheath 30 may have a proximalmost end 34 of slightly tapering diameter. The diminished end of the sheath 34 as shown in FIGS. 1, 2, and 3 is arranged to slipfit into a Luer lock 35 but may be slipfit directly into the needle stop assembly 12. A connector means 40 is disposed on the distalmost end of the needle stop assembly 12. The connector means 40 has a bore 42 therethrough through which the needle 16 extends. The connector means 40 engagably becomes part of a hub 44. The hub 44 has a central core 46 of cylindrical configuration. The bore 42 extends through the core 46. The core 46 extends generally the longitudinal distance of the hub 44. An internal arrangement of screw threads 48 is disposed about the core 46 having a space therebetween. Slidably disposed on the needle 16 and proximal to the hub 44 is a generally cone-shaped bushing 50 of conical configuration. The bushing 50 has a longitudinally directed bore 52 through which the needle 16 extends. A hollow housing 54 is disposed coaxially adjacent the bushing 50. The housing 54 has a hollow cone-shaped central opening 56. A bore 58 extends through the proximalmost end of the housing 54. The bore 58 receives the needle 16.

In operation of the needle assembly 10 the needle 16 is withdrawn in the sheath 30 so that the distal portion of the needle 16 is adjacent the particular graduation 32 which comprises the depth of needle penetration desired. At that point, the needle 16 is held at that location and the housing 54 is rotatively threaded into the internal threads of the hub 44.

The housing 54 has an arrangement of external threads 60 which mate with the internal threads 48 of the housing 44. A plurality of tabs 64 are disposed on the proximalmost end of the housing 54. The tabs 64 facilitate manual rotation of the housing 54 into and out of the hub 44.

Threaded advancement of the housing 54 into the hub 44 causes the elastomer bushing 50 to be compressed as it is received into the opened core 56 of the housing 54. This causes radially inwardly directed compression of the bushing 50 onto the needle 16 at that peripheral location. This causes the locking effect of the needle with respect to the needle stop assembly 12. Thus the needle may be inserted into a patient up to the point of the needle stop assembly 12 with the foreknowledge that the depth setting is accurate.

Thus there has been shown a needle stop assembly which may be set to an infinite variety of depths and which stop assembly of sterile construction and which may be easily manipulated and changed at will.

It is intended that the appended claims be interpreted as exemplary only.

I claim:

1. A biological needle assembly having a depth setting and stop arrangement thereon, comprising:
    an elongated needle;
    a connector means at the proximal end of the needle;
    a needle stop assembly arranged with the connector at the proximal end of a needle; and
    a sheath assembly having graduations thereon to effectuate the proper depth setting of said needle with respect thereto;
    said needle stop assembly comprising a threadably adjustable compressive arrangement which locks said needle thereto, which includes a radially inwardly directed gripping means which can be tightened and untightened to permit the passage of the needle therethrough, comprising a hub and a housing which are coaxially arranged about a centrally disposed needle, and a centrally disposed bushing arranged therebetween, said bushing being receivable within said housing and engagable against one end of a portion of said hub.

2. The needle asembly as recited in claim 1, wherein said housing and said hub are threadably receivable with one another and which act to capture and compress the bushing therebetween.

3. The needle arrangement as recited in claim 2, wherein said bushig is compressed peripherally inwardly onto said needle shaft when said housing and said hub are tightened toward one another.

4. A method of adjusting a needle for its depth setting, comprising:
    arranging a needle in a sheath assembly having graduations marked thereon;
    providing a hub on the proximalmost end of said needle;
    providing a threadable compressible needle stop assembly between said sheath and said hub;
    moving said needle with respect to said sheath; and
    rotating said needle stop assembly so as to provide compressive forces onto the periphery of said needle to effectuate a stop means thus setting the depth of the needle to be utilized in a patient, said stop assembly comprising a hub and a housing with a bushing therebetween, the threaded advance of said housing into said hub causing said compression of the bushing about said needle.

* * * * *